United States Patent
Weeber et al.

(10) Patent No.: US 9,572,657 B2
(45) Date of Patent: Feb. 21, 2017

(54) MICRO-INCISION IOL AND POSITIONING OF THE IOL IN THE EYE

(71) Applicant: AMO Groningen B.V., Groningen (NL)

(72) Inventors: Hendrik A. Weeber, Groningen (NL); Sverker Norrby, Leek (NL); Marrie H. Van Der Mooren, Engelbert (NL); Luuk Franssen, Groningen (NL)

(73) Assignee: AMO Groningen B.V., Groningen (NL)

( * ) Notice: Subject to any disclaimer, the term of this patent is extended or adjusted under 35 U.S.C. 154(b) by 0 days.

(21) Appl. No.: 14/196,658

(22) Filed: Mar. 4, 2014

(65) Prior Publication Data

US 2014/0277434 A1    Sep. 18, 2014

Related U.S. Application Data

(60) Provisional application No. 61/779,505, filed on Mar. 13, 2013.

(51) Int. Cl.
*A61F 2/16* (2006.01)

(52) U.S. Cl.
CPC .............. *A61F 2/1656* (2013.01); *A61F 2/161* (2015.04); *A61F 2/1648* (2013.01); *A61F 2002/1681* (2013.01); *A61F 2220/0016* (2013.01)

(58) Field of Classification Search
CPC ........ A61F 2/16; A61F 2/1613; A61F 2/1629; A61F 2/1635; A61F 2/1486; A61F 2/161
USPC .............................. 623/6.18, 6.45, 6.13, 6.36
See application file for complete search history.

(56) References Cited

U.S. PATENT DOCUMENTS

| | | | |
|---|---|---|---|
| 4,172,297 A * | 10/1979 | Schlegel | A61F 2/16 623/6.17 |
| 5,171,320 A | 12/1992 | Nishi | |
| 5,266,074 A | 11/1993 | Nishi et al. | |
| 6,027,531 A | 2/2000 | Tassignon | |
| 2006/0047340 A1* | 3/2006 | Brown | 623/6.13 |
| 2006/0069433 A1* | 3/2006 | Nun | 623/6.45 |

FOREIGN PATENT DOCUMENTS

| | | |
|---|---|---|
| EP | 2422746 A1 | 2/2012 |
| WO | WO-02065951 A2 | 8/2002 |

OTHER PUBLICATIONS

Dick H.B., et al., "Intraocular Lens Fixated in the Anterior Capsulotomy Created in the Line of Sight by a Femtosecond Laser," Journal of Refractive Surgery, 2014, vol. 30(3), pp. 198-201.
International Search Report and Written Opinion for Application No. PCT/IB2014/000831, mailed on Nov. 13, 2014, 11 pages.

(Continued)

*Primary Examiner* — David H Willse
*Assistant Examiner* — Tiffany Shipmon
(74) *Attorney, Agent, or Firm* — Abbott Medical Optics Inc.

(57) ABSTRACT

An intraocular lens that is capable of being inserted through a micro-incision includes an optic having an anterior and a posterior surface and a plurality of projections extending from the anterior and posterior surfaces. The anterior and posterior surfaces include a recess. The optic is implanted such that a rim of the capsulorhexis is disposed in the recess such that the plurality of projections grip the capsular bag.

8 Claims, 5 Drawing Sheets

(56) References Cited

OTHER PUBLICATIONS

Dick H.B., et al., "Femtosecond Laser—Assisted Technique for Performing Bag-in-the-Lens Intraocular Lens mplantation," Journal of Cataract Refract Surgery, 2013, vol. 39 (9), pp. 1286-1290.
Tassignon M.J., et al., "Clinical Outcomes of Cataract Surgery after Bag-in-the-Lens Intraocular Lens Implantation Following ISO Standard 11979-7:2006," Journal of Cataract Refract Surgery, 2011, vol. 37 (12), pp. 2120-2129.

* cited by examiner

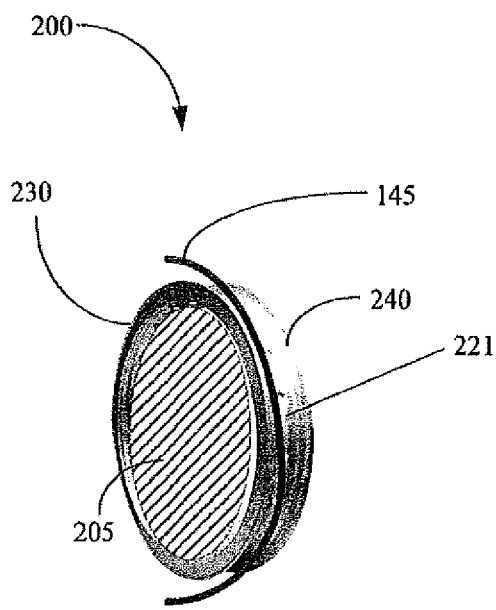
Figure 2C
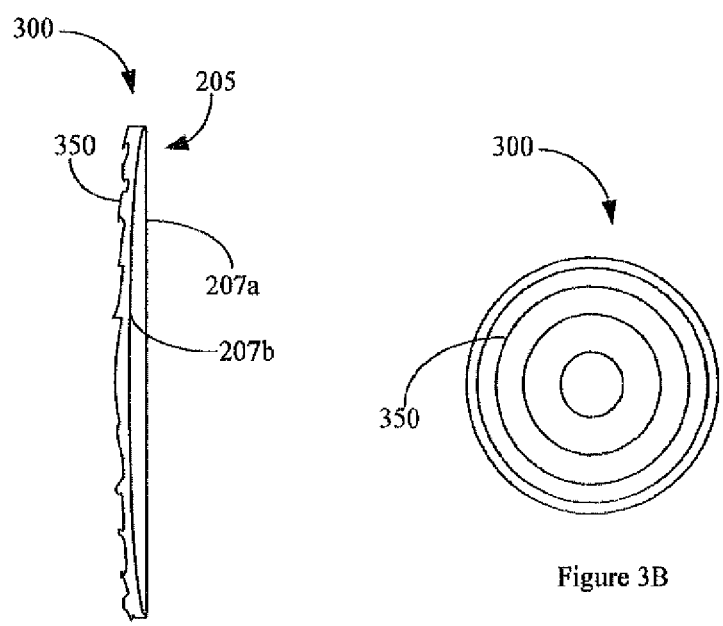
Figure 3A
Figure 3B

MICRO-INCISION IOL AND POSITIONING OF THE IOL IN THE EYE

CROSS-REFERENCES TO RELATED APPLICATIONS

This application claims priority to U.S. Provisional Application No. 61/779,505 filed on Mar. 13, 2013, the entire contents of which are incorporated herein by reference.

BACKGROUND

Field of the Invention

This invention relates generally to intraocular lenses, and more specifically, to compact intraocular lenses that can be implanted in the eye with a micro-incision.

Description of the Related Art

A human eye can suffer diseases that impair a patient's vision. For example, a cataract can increase the opacity of the lens, ultimately leading to blindness. To restore the patient's vision, the diseased lens may be surgically removed and replaced with an artificial lens, known as an intraocular lens, or IOL. As another example, to treat eye conditions such as myopia, hypermetropia or presbyopia, an intraocular lens can be surgically implanted in the eye to replace or supplement the natural eye.

IOLs can be inserted in the eye through an incision in the eye. The incision size can depend on the material of the IOL, size and structure of the IOL and the mode in which the IOL is delivered in the eye. For example, the incision size can be about 10-12 mm in standard extracapsular surgery, about 5.5-7.0 mm in manual small incision surgery and about 3.0-5.5 mm if phacoemulsification methods are used. Reducing the size of the incision can reduce the complexity of the surgical procedure, reduce post-surgical recovery time and reduce patient discomfort. IOLs that can be implanted in the eye through micro-incisions can advantageously increase patient safety, reduce recovery time and patient discomfort.

SUMMARY

IOLs can be implanted in the eye to correct for a variety of vision defects. IOLs can be introduced in the eye through an incision made in the corneal layers and implanted in the capsular bag or in front of the capsular bag. Conventional IOL designs and insertion procedures enable IOLs to be inserted through incisions that range in size between 3.0 mm-12 mm. While conventional IOLs and methods of implantation provide the end result of treating the vision conditions in question, it is advantageous to reduce the size of the incision made to access the inside of the eye. Smaller incisions will reduce the complexity of the surgical procedure, reduce post-surgical recovery time and reduce patient discomfort. Certain embodiments disclosed herein include compact IOLs that are capable of being inserted through micro-incisions, such as, for example incisions that are a few hundred microns in size.

Embodiments of the IOLs disclosed herein comprise an optic adapted to focus light on the retina when disposed in the eye and a haptic or mounting structure that is operably coupled to the optic. In one aspect the haptics can be small and soft such that the IOL can be folded or rolled so as to occupy a smaller volume as compared to current IOL designs.

In another aspect, the optic of the IOL embodiments disclosed herein can be configured to be in tension when deployed in the eye, e.g., subject to stretching forces applied transverse to the optical axis of the IOL, which can maintain a thin deployed configuration that retains its structural integrity.

In another aspect, an intraocular lens comprises an optic disposed about an optical axis, the optic having an anterior surface and a posterior surface with at least one anterior projection coupled to and extending radially from the optic and at least one posterior projection adjacent to the at least one anterior projection, wherein the at least one posterior projection is coupled to and extends radially from the optic. The anterior and posterior projections are resiliently biased such that distal ends of the anterior projection and the posterior projection can be moved away from and toward each other. When implanted, the distal ends of at least one of the anterior projection and the posterior projection is configured to grip at least one of an outside surface and an inside surface adjacent to a capsulorhexis on an anterior portion of an evacuated capsular bag. At least one of the surfaces may include a diffractive surface. In addition, the anterior and posterior projection may be actuated by axially compressing a zone disposed between the optic and distal ends of the anterior and/or posterior projection. When implanted in the eye, the optic may be subject to stretching force applied transverse to the optical axis. The stretching force may be distributed uniformly across the surface of the optic. In addition, there may be a recess between the anterior and posterior projections. The recess may have protrusions for securing the IOL to the capsular bag, and the protrusions may be shaped as barbs or teeth. When implanted, the rim of the capsulorhexis may be disposed in the recess. When implanted in the eye, the optic is partially in the capsular bag and partially outside the capsular bag.

Details of one or more implementations of the subject matter described in this specification are set forth in the accompanying drawings and the description below. Other features, aspects, and advantages will become apparent from the description, the drawings, and the claims. The drawings depicting novel and non-obvious aspects of the invention are for illustrative purposes only. Note that the relative dimensions of the following figures may not be drawn to scale.

BRIEF DESCRIPTION OF THE DRAWINGS

The drawings include the following figures in which like numerals refer to like parts.

FIG. 2C is a perspective view of another implementation of an IOL that can be mounted on the anterior portion of the capsular bag.

FIG. 3A illustrates a side view of a diffractive optic included in the IOL illustrated in FIG. 2A. FIG. 3B illustrates the front view of the diffractive optic illustrated in FIG. 3A.

DETAILED DESCRIPTION OF THE PREFERRED EMBODIMENT

It is to be understood that the figures and descriptions of the present invention have been simplified to illustrate elements that are relevant for a clear understanding of the present invention, while eliminating, for the purpose of clarity, many other elements found in typical lenses, lens systems and lens design methods. Those of ordinary skill in the arts may recognize that other elements and/or steps are desirable and may be used in implementing the embodiments described herein.

Figure 1:
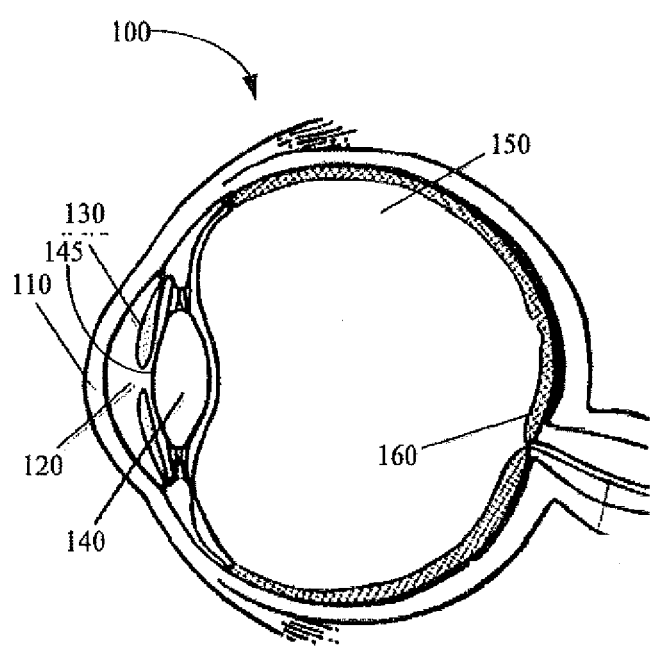
FIG. 1 is a diagram illustrating the relevant structures of the human eye.

FIG. 1 is a schematic drawing of a human eye 100. Light enters the eye from the left of FIG. 1, and passes through the cornea 110, the anterior chamber 120, a pupil defined by the iris 130, and enters the lens 140. After passing through the lens 140, light passes through the vitreous chamber 150, and strikes the retina 160, which detects the light and converts it to a signal transmitted through the optic nerve to the brain (not shown).

The natural lens 140 is a transparent crystalline biconvex optic that is housed in a structure known as the capsular bag 145. The lens 140 can focus light from objects over a wide range of distances on the retina by changing its shape thereby changing its focal length. The ability of the lens 140 to change its shape to adjust the focal length is known as accommodation. During accommodation, the natural lens 140 is acted on by ocular forces generated by ciliary muscles, zonular fibers (also known as zonules) and the capsular bag. For example, the ciliary muscles and the zonular fibers can pull on the capsular bag to change its shape. The motion of the capsular bag generally deforms the natural lens 140 in order to change its refractive power and/or the location of the lens 140, so that the eye can focus on objects at varying distances away from the eye.

To treat patients suffering from various eye diseases such as myopia, hypermetropia, presbyopia, cataract, etc., an intraocular lens (IOL) is inserted into the eye to replace or augment the natural lens 140. The IOLs can be configured such that they can be rolled and/or compacted prior to insertion and inserted into the eye through incisions that range in size between 3.0 mm-12.0 mm. The IOLs can be configured to unroll and/or expand after insertion into the eye. The IOL can be introduced in the eye through an incision made in the corneal layers and implanted either in the capsular bag 145 or in front of the capsular bag 145 or partly in the capsular bag 145 and partly outside the capsular bag 145. To implant the IOL either partially or completely in the capsular bag 145, the diseased natural lens 140 can be removed from the eye by a process known as phacoemulsification. During phacoemulsification, an opening is created in the anterior portion of the capsular bag 145 by a process known as capsulorhexis and the diseased lens is removed. In various implementations, a pulsed laser (e.g. a femtosecond laser) can be used to create an opening in the anterior portion of the capsular bag 145 by ablating a pattern onto the desired area of the capsular bag 145. The capsulorhexis produced by pulsed lasers can be highly reproducible. The energy, frequency and the duty cycle of the pulsed lasers can be varied to produce a capsulorhexis that is precisely sized and shaped to suit the needs of the patient. The use of pulsed laser in capsulorhexis can reduce the incidence of tears in the capsular bag 145 which can aid in maintaining the strength and the integrity of the capsular bag 145. Pulsed lasers can be also used to create openings that are regularly shaped and well-centered. A well-centered and regularly shaped capsulorhexis can reduce the possibility of the IOL being decentered or tilted which can adversely affect the quality of vision. Additionally, the edge of the capsulorhexis produced by pulsed lasers can be smooth such that the vision through the IOL is not impacted.

IOLs designed for placement in the capsular bag are generally of a volume requiring an incision of significant size. For example, the IOL can be bulky such that it is properly anchored in the capsular bag and does not get decentered or tilted during operation. As another example, some accommodating IOL designs are intended to substantially fill the capsular bag in operation. While there are good reasons for such designs, such as to more closely mimic the natural eye function and to avoid a shrink-wrapping effect of the evacuated capsular bag, the net result is either a larger incision size or a much more complex injector system to minimize incision size growth. These and other issues can result in a patient being subject to incisions in the range of 3.0-12.0 mm for the placement of an IOL. As discussed above, it is advantageous to design IOLs that can be inserted through an incision smaller than 3.0 mm, for example, incisions in the range of about 100 µm to about 1 mm.

The embodiments of IOLs disclosed herein are configured to be implanted partially in the capsular bag 145 and partially outside the capsular bag 145. In particular the embodiments of the IOLs disclosed herein are configured to be disposed on the rim of the capsulorhexis. The embodiments of the IOLs disclosed herein include soft and compact haptics that allow the IOLs to be inserted in the eye through micro-incisions. Furthermore, the soft and compact haptics are configured to grip, clip, clasp or clamp onto the rim of the capsulorhexis. Various implementations of the IOLs described herein also include thin and compact optics that can retain their structural integrity when maintained under tension. The optic of the IOL embodiments disclosed herein can be configured to be in tension when deployed in the eye, e.g., subject to stretching forces applied transverse to the optical axis of the IOL.

Figure 2A:
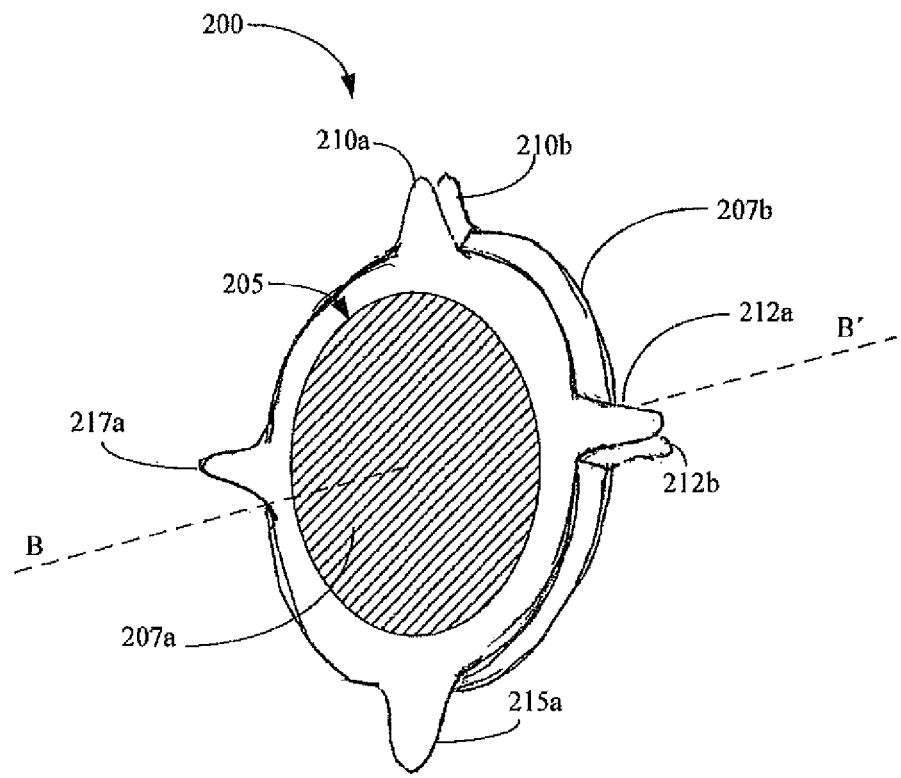
FIG. 2A is a perspective view of an implementation of an IOL that can be mounted on the anterior portion of the capsular bag.
Figure 2B:
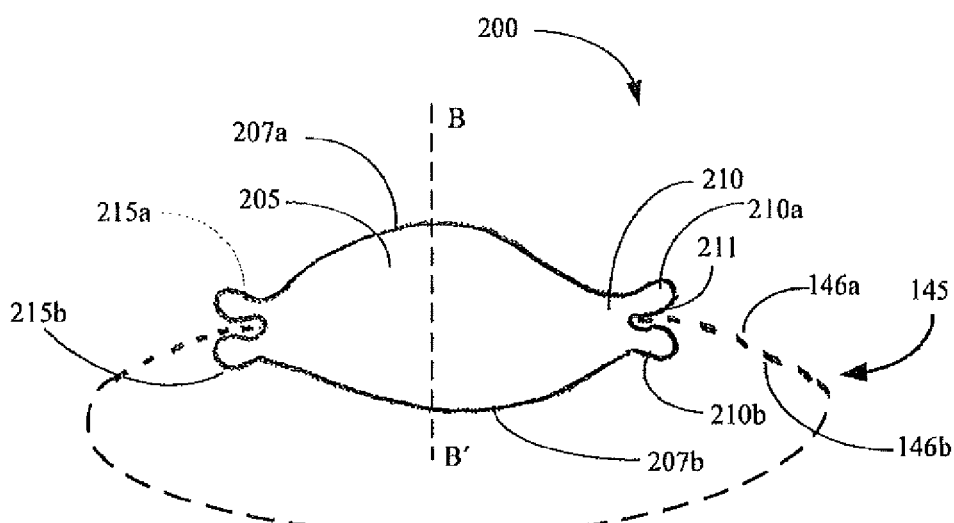
FIG. 2B is a cross-sectional view of the IOL illustrated in FIG. 2A as mounted on a portion of the anterior portion of the capsular bag.

FIG. 2A is a perspective view of an implementation of an IOL that can be mounted on the anterior portion of the capsular bag, for example, on the rim of the capsulorhexis. FIG. 2B is a cross-sectional view of the IOL illustrated in FIG. 2A as mounted on the anterior portion of the capsular bag. The IOL 200 includes an optic 205 intersected by an optical axis B-B'. The optic 205 can include an optically transmissive and a deformable material, such as, for example, acrylic, silicone, PMMA, PDMS, hydro-siloxane, etc. In various implementations, the optic 205 may be implanted in the eye such that the optic is maintained under tension or is stretched and has a thickness between about 100 µm and 1.5 mm along the optical axis B-B'. In various implementations, the optic 205 can have a biconvex shape, a meniscus shape, a plano-convex shape, a plano shape, etc. The optic 205 has an anterior surface 207a facing the iris 130 of the eye and a posterior surface 207b opposite the anterior surface 207a. The anterior surface 207a and/or or the posterior surface 207b can be curved such that the optic 205 has a refractive power. In various implementations, the anterior surface 207a and/or the posterior surface 207b can include diffractive features such that the optic 205 has a diffractive power. Particular implementations of diffractive optics are discussed below with reference to FIGS. 3A and 3B below. In various implementations, the optic 205 can be monofocal, bifocal or multifocal. In some implementations, the optic 205 can include antireflective coatings and/or coatings that reduce glare. In various implementations, the IOL 200 can include a plurality of optics. For example, in some embodiments, the IOL 200 can be a dual optic.

The IOL 200 includes a plurality of projections 210*a*, 210*b*, 212*a*, 212*b*, 215*a*, 215*b*, 217*a* and 217*b* that are disposed along the periphery of the optic 205 and extend outward from the optic, preferably from the anterior surface 207*a* and the posterior surface 207*b* of the optic 205. The plurality of projections can be arranged in pairs (e.g. 210*a* and 210*b*, 212*a* and 212*b*, 215*a* and 215*b*, 217*a* and 217*b*) such that every projection that extends from the anterior surface 207*a* has a corresponding projection that extends from the posterior surface 207*b*. Each pair of projections includes a groove or a recess 211 between them. In various implementations the groove or recess 211 can include a curved surface. The groove or recess 211 is configured to receive a part of the anterior portion of the capsular bag 145 such that each pair of projections (210*a* and 210*b*, 212*a* and 212*b*, 215*a* and 215*b*, 217*a* and 217*b*) clasp, grasp, grip or clip onto the rim of the capsulorhexis. For example, as shown in FIG. 2B, a first part of the anterior portion of the capsular bag 145 that forms the rim of the capsulorhexis is disposed in the recess 211. The first part of the anterior portion of the capsular bag is pinched or sandwiched between the two projections 210*a* and 210*b* when the capsular bag is so positioned. Similarly, the projections 215*a* and 215*b* of the haptic structure 215 pinch or sandwich a second part of the anterior portion of the capsular bag 145 that forms the rim of the capsulorhexis. When a part of the capsular bag 145 is inserted into the groove or recess 211 the anterior projection 210*a* grips on to the front surface of the anterior portion of the capsular bag 145 and the posterior projection 210*b* grips on to the rear surface of the anterior portion of the capsular bag 145.

In some implementations, each projection can be an individual structure that is attached to the anterior surface 207*a* r the posterior surface 207*b* of the optic 205. For example, with reference to FIG. 2A, projections 210*a*, 212*a*, 215*a* and 217*a* extend from the anterior surface 207*a* of the optic 205 and the projections 210*b*, 212*b*, 215*b* and 217*b* extend from the posterior surface 207*b* of the optic 205. In some implementations, the pair of projections can be a part of a bifurcated haptic structure. For example, with reference to FIG. 2B, the pair of projections 210*a* and 210*b* can be a part of a bifurcated haptic structure 210 that extends from the periphery of the optic 205.

In the implementation illustrated in FIG. 2A, the plurality of projections 210*a*, 212*a*, 215*a* and 217*a* (or the plurality of projections 210*b*, 212*b*, 215*b* and 217*b*) are arranged around the anterior surface 207*a* (or the posterior surface 207*b*) of the optic 205 such that adjacent projections are disposed approximately at right angles with each other. Stated another way, when viewed from the front, an angle of about 90 degrees is defined between lines extending out from a central optical axis of the surface 207*a* to the circumferential mid-point of nearest neighboring projections. However, in other embodiments, the plurality of projections 210*a*, 212*a*, 215*a* and 217*a* (or the plurality of projections 210*b*, 212*b*, 215*b* and 217*b*) can be arranged such that adjacent haptic structures are disposed at angles less than or greater than 90 degrees with each other. Although, in the embodiment shown in FIG. 2A four projections extend from the anterior surface 207*a* and the posterior surface 207*b*, in other embodiments one, two, three, five, six, eight, twelve or more projections can extend from each surface of the optic. In various implementations, the plurality of anterior projections may be united to form a continuous anterior ring 230 that is disposed around the anterior surface 207*a* of the optic 205 as illustrated in FIG. 2C. Similarly the plurality of posterior projections may be united to form a continuous posterior ring 240 that is disposed around the posterior surface 207*b* of the optic 205 as illustrated in FIG. 2C. The anterior and posterior rings can include a continuous groove or recess 221 as shown in FIG. 2C.

As noted above, the IOL 200 is intended to be insertable through a micro-incision. As such, the material of the optic 205, the material of the plurality of projections, the dimensions of the optic 205 and the size of the plurality of projections are preferably selected such that the IOL 200 can be rolled, folded and/or compacted to have a small volume, for example, between about 10 mm$^3$ and 40 mm$^3$ to allow insertion through a micro-incision. To facilitate insertion of the IOL, the plurality of projections is preferably configured to occupy a low profile for delivery through such an incision. For example, plurality of projections can be small and have a linear dimension that is in the range of about 0.2 mm and about 1.5 mm.

The IOL 200 can be attached to the evacuated capsular bag 145 after phacoemulsification. In one method of attachment, the IOL 200 is placed over the opening created in the capsular bag 145 during phacoemulsification such that the portion of the capsular bag 145 that forms the rim of the capsulorhexis is inserted into the groove 211 such that the anterior projections 210*a*, 212*a*, 215*a* and 217*a* are adjacent the front surface of the anterior portion of the capsular bag 145 and the posterior projections 210*b*, 212*b*, 215*b* and 217*b* are adjacent the rear surface of the anterior portion of the capsular bag 145. The IOL 200 is mechanically attached to the rim of the anterior surface of the capsular bag 145 by bringing the plurality of projections toward the front and rear surface of the anterior portion of the capsular bag 145 such that the plurality of projections grips the anterior portion of the capsular bag 145. In various implementations, the IOL 200 can be placed over the opening created in the capsular bag 145 such that a part of the IOL 200 is inside the evacuated capsular bag 145 and a part of the IOL 200 is outside the evacuated capsular bag 145.

In various implementations, the plurality of projections 210*a*, 210*b*, 212*a*, 212*b*, 215*a*, 215*b*, 217*a* and 217*b* can include a soft bio-compatible elastic material to facilitate the attachment of the optic 205 to the rim of the capsulorhexis. Various implementations of the IOL 200 can be formed such that in the resting or natural state, the pair of projections 210*a* and 210*b*, 212*a* and 212*b*, 215*a* and 215*b*, 217 and 217*b* can be configured to be in contact with each other. In such implementations, each pair of projections 210*a* and 210*b* can be held in contact with each other by a spring force resulting from the shape and the material of the projections. In some such implementations, each pair of projections 210*a* and 210*b* can be held in contact with each other by adhesive forces (e.g. hydrophilic attractive force, chemical stiction forces, etc.). When such implementations are implanted in the eye, a parting force (e.g. force applied by forceps) can be applied to space apart each pair of projections from each other and a part of the capsular bag 145 is inserted into the groove or recess 211. Subsequently, when the parting force is removed, the projections clasp on to the part of the inserted capsular bag 145 due to the tendency of the projections to return to their initial resting state.

Some implementations of the IOL 200 can be formed such that in the resting or natural state, each pair of projections are spaced apart from each other. In such implementations, when the IOL 200 is implanted in the eye a part of the capsular bag 145 is inserted in the recess 211. Subsequently a pinching force (e.g. force applied by forceps) is applied to bring each pair of projections toward each other such that the part of the inserted capsular bag is securely pinched or sandwiched between each pair of projections. In various implementations, the pair of projections can be laser welded together after implantation to more securely attach the optic.

Figure 5A:
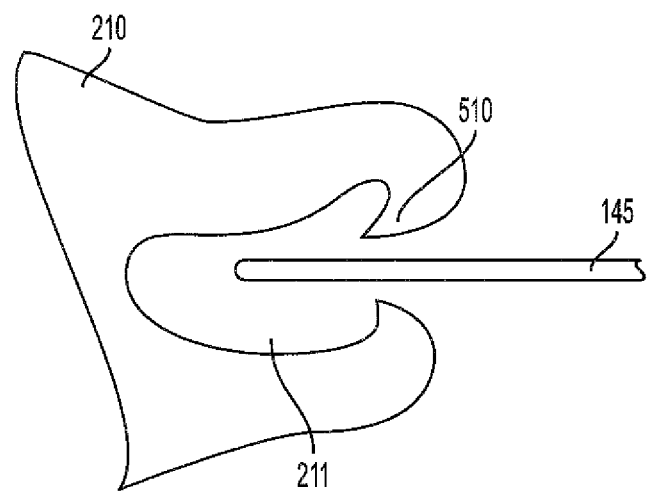
FIGS. 5A and 5B are cross-sectional views showing the exemplary recesses for the IOL illustrated in FIG. 2A.
Figure 5B:
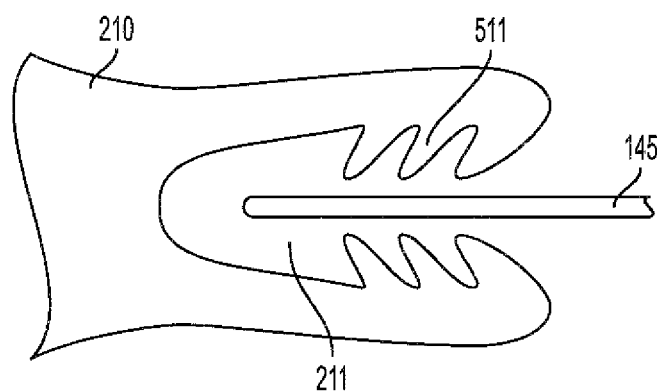

As seen in FIGS. 5A and 5B, the recess 211 can have detailed geometries, in order to maximize the clamping and stretching geometry, as well as ease IOL implantation. The preferred embodiments maximize the grip onto the capsular bag 145, through teeth-like protrusions 510 and 511, which function as gentle barbs to hold the IOL to the capsular bag.

In various implementations, the optic 205 can be maintained under tension when implanted in the eye. For example, in one method of implantation, the optic 205 can be attached to a first part of the rim of the capsulorhexis, as described above. Subsequently, the IOL 200 can be stretched to attach to a second part of the rim of the capsulorhexis. The optic 205 is thus subject to stretching forces that are applied transverse to the optical axis B-B'. Since, the optics 205 can be maintained under tension, the optic 205 can have a slim profile while still have structural integrity. In other words, the optic 205 can be made thinner than optics for accommodating IOLs which have a certain minimum thickness in order to have structural stability during accommodation. Such optics can be advantageously inserted through micro-incisions. Another possible advantage of the various implementations of IOL 200 discussed above, is that they can be relatively insensitive to tilt or decentering as compared to other accommodating IOLs that are mounted in the capsular bag 145.

Based on the distribution of the plurality projections, the optic 205 can be stretched symmetrically or asymmetrically in various radial directions. For example, the optic 205 can be symmetrically stretched in all radial directions, if the projections are uniformly distributed along the entire periphery of the optic 205 with sufficiently high density. However, if the projections are not uniformly distributed along the entire periphery of the optic 205 or if the density of the projections is small (e.g. two projections, four projections, etc.) then the optic 205 can be asymmetrically stretched in different directions. Asymmetrical stretching can be advantageous to provide toric or multifocal lenses where different portions of the optic 205 can be stretched differently to provide different add powers. The different add powers can be at different diameters of the optic 205 to eliminate or induce astigmatism or can be configured to provide multiple foci for viewing a combination of near, intermediate, and far.

As discussed above, the optic 205 can have a slim profile to allow insertion through micro-incisions. In such implementations, it may not be practical to provide high refractive power. Accordingly, optics with slim profiles can include diffractive features to provide additional diffractive power when the refractive power provided by such optics is not sufficient to suit the patient's needs. FIGS. 3A and 3B illustrate implementations of a diffractive lens 300 that can provide diffractive power. The diffractive lens 300 includes an optic 205 with a slim profile and a plurality of diffractive features 350. The diffractive features 350 can be disposed on the anterior surface 207a of the optic 205 or the posterior surface 207b of the optic 205 or both the anterior and the posterior surfaces. The diffractive features 350 can include a plurality of surface relief features or volume features. In various implementations, the diffractive features 350 can be embossed, etched or printed directly on the surface of the optic. In other implementations, a coating including the diffractive features 350 can be laminated onto the surface of the optic 205.

The diffractive lens 300 can be configured as a thin optical element that can be maintained under tension while still maintaining structural integrity. The plurality of diffractive features 350 can be arranged as a plurality of concentric zones, with spacings between adjacent zones progressively decreasing at increasing distance away from the center of the diffractive lens 300. The amount of diffractive power provided by the diffractive lens 300 is determined in part by the zone diameters. Within each zone, the surface profile has a particular profile height, which may or may not be constant throughout the zone. For instance, the surface profile may increase in height from the inside to the outside of the zone.

A specific example of a slim diffractive profile is a multi order diffractive lens. Such lenses are described in U.S. Pat. No. 5,589,982. The combination of this thin diffractive lens and an attachment to the capsular bag has specific advantages. Because of the capsular attachment, the optic may be subjected to stretching forces only. This is in contrast to the compressive forces, in optics being positioned in the capsular bag using the traditional haptics (the haptics are compressed in the capsular bag, and these compressive forces are guided through the optic). As a result, in the current invention, the optic can be made extremely thin, without losing structural stability. Consequently, the thin lens can have the shape of a thin film, being stretched across the capsulorhexis opening.

Figure 4:
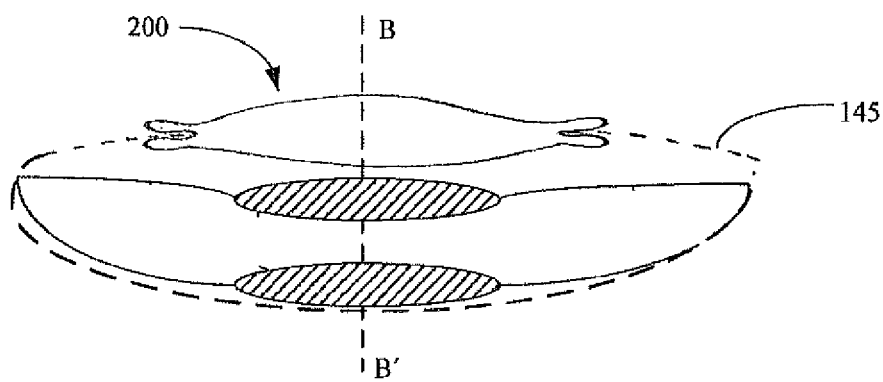
FIG. 4 illustrates a cross-sectional view of the IOL illustrated in FIG. 2B mounted on the capsular bag in conjunction with a dual optic IOL mounted in the capsular bag.

In various implementations, the capsulorhexis mounted IOL 200 can be implanted in the eye along with another IOL that is implanted in the capsular bag 145 or in front of the capsular bag 145. By way of example, FIG. 4 illustrates a cross-sectional view of the capsulorhexis mounted IOL 200 illustrated in FIGS. 2A-3B mounted on the capsular bag along with a dual optic IOL located in the capsular bag 145. In such implementations the capsulorhexis mounted IOL 200 can augment the visual effects provided by another IOL implanted in the eye. For example, in various implementations, the capsulorhexis mounted IOL 200 can provide additional add power that improves the vision of the patient. As another example, in some implementations, the capsulorhexis mounted IOL 200 can correct for defects and aberrations that result after another IUL is implanted in the eye.

Although the invention has been described and pictured in an exemplary form with a certain degree of particularity, it should be understood that the present disclosure of the exemplary form has been made by way of example, and that numerous changes in the details of construction and combination and arrangement of parts and steps may be made without departing from the spirit and scope of the invention as set forth in the claims hereinafter.

What is claimed is:
1. An intraocular lens comprising:
an optic disposed about an optical axis, the optic having an anterior surface, a posterior surface, and a recess extending along a periphery of the optic between the anterior and posterior surfaces, wherein the recess includes protrusions;
at least two anterior projections coupled to and extending radially from the optic; and
at least two posterior projections coupled to an extending radially from the optic, wherein each posterior projection is adjacent to a particular one of the anterior projections, wherein the anterior and posterior projections are resiliently biased such that distal ends of the anterior projections and the posterior projections can be moved away from and toward each other, and wherein, when implanted, the distal ends of the anterior projections and the posterior projections are configured to grip at least one of an outside surface and an inside surface adjacent to a capsulorhexis on an anterior portion of an evacuated capsular bag.

2. The intraocular lens of claim 1, wherein the anterior and posterior projection is actuated by axially compressing a zone disposed between the optic and distal ends of the anterior and/or posterior projection.

3. The intraocular lens of claim 1, wherein, when implanted in the eye, the optic is subject to a stretching force applied transverse to the optical axis.

4. The intraocular lens of claim 3, wherein the stretching force is distributed uniformly across the surface of the optic.

5. The intraocular lens of claim 1, wherein the recess is disposed between the anterior and posterior projections.

6. The intraocular lens of claim 5, wherein, when implanted, the rim of the capsulorhexis is disposed in the recess.

7. The intraocular lens of claim 1, wherein the protrusions are teeth-like.

8. The intraocular lens of claim 1, wherein, when implanted in the eye, the optic is located partially in the capsular bag and partially outside the capsular bag.

* * * * *